United States Patent
Bashan et al.

(10) Patent No.: US 12,426,557 B2
(45) Date of Patent: Sep. 30, 2025

(54) SYSTEM AND METHOD OF GROWING ALGAE USING GEOTHERMAL GAS

(71) Applicant: Vaxa Technologies Ltd., Rosh Pinna (IL)

(72) Inventors: Ohad Bashan, Sde Varburg (IL); Isaac Berzin, Jerusalem (IL); Oded Bashan, Rosh Pina (IL)

(73) Assignee: Vaxa Technologies Ltd., Rosh Pinna (IL)

(*) Notice: Subject to any disclaimer, the term of this patent is extended or adjusted under 35 U.S.C. 154(b) by 727 days.

(21) Appl. No.: 17/844,267

(22) Filed: Jun. 20, 2022

(65) Prior Publication Data
US 2022/0322626 A1   Oct. 13, 2022

Related U.S. Application Data

(63) Continuation-in-part of application No. 16/761,665, filed as application No. PCT/IL2018/051177 on Nov. 5, 2018, now abandoned.
(Continued)

(51) Int. Cl.
*A01G 33/00* (2006.01)
*C12M 1/00* (2006.01)
(Continued)

(52) U.S. Cl.
CPC ............ *A01G 33/00* (2013.01); *C12M 23/06* (2013.01); *C12M 29/24* (2013.01); *C12N 1/12* (2013.01)

(58) Field of Classification Search
CPC .... B01D 53/52; B01D 2259/80; C12M 21/04; C12M 21/02; C12M 25/14; C12M 25/06;
(Continued)

(56) References Cited

U.S. PATENT DOCUMENTS 5,151,347 A    9/1992  Delente et al.
2008/0160591 A1  7/2008  Willson et al.
(Continued)

FOREIGN PATENT DOCUMENTS

EP    1801197    6/2007
KR    20150006718   1/2015

*Primary Examiner* — Michael L Hobbs
(74) *Attorney, Agent, or Firm* — PEARL COHEN ZEDEK LATZER BARATZ LLP

(57) ABSTRACT

A method of growing algae in a cultivation container is disclosed. In some the method may include: circulating, via the cultivation container, in a closed loop, a first predetermined amount of gas mixture comprising a first type of gas and at least one second type of gas, the gas mixture may enter the container via one or more entrance spargers and exit via at least one exit pipe, the first type of gas may contain $CO_2$ at a known first amount; receiving signal indicative of the amount of $CO_2$ or $H_2S$, in the gas mixture; when the signal indicates that the amount of $CO_2$ drops below a first predetermined level or when the signal indicates that the amount of $H_2S$ rises above a first predetermined level, extracting a second predetermined amount of the gas mixture from the cultivation container: and adding an amount of the first type of gas to the gas mixture, equal to the second predetermined amount.

20 Claims, 2 Drawing Sheets

Related U.S. Application Data

(60) Provisional application No. 62/581,789, filed on Nov. 6, 2017.

(51) Int. Cl.
*C12M 1/12* (2006.01)
*C12N 1/12* (2006.01)

(58) Field of Classification Search
CPC ...... C12M 29/06; C12M 47/18; C12M 23/06; C12M 41/34; A01G 33/00; C12N 1/12
See application file for complete search history.

(56) References Cited

U.S. PATENT DOCUMENTS

| | | |
|---|---|---|
| 2012/0107792 A1* | 5/2012 | Babbitt .................. C12M 21/02 435/3 |
| 2012/0107921 A1 | 5/2012 | Willson et al. |
| 2013/0059369 A1 | 3/2013 | Lin et al. |
| 2014/0024091 A1 | 1/2014 | Reed et al. |
| 2021/0179986 A1 | 6/2021 | Bashan et al. |

* cited by examiner

SYSTEM AND METHOD OF GROWING ALGAE USING GEOTHERMAL GAS

CROSS REFERENCE TO RELATED APPLICATIONS

This application is a Continuation-In-Part of prior U.S. application Ser. No. 16/761,665, entitled "SYSTEM AND METHOD OF GROWING ALGAE USING GEOTHERMAL GAS" which in turn is a National Phase Application of International Application No. PCT/IL2018/051177 filed on Nov. 5, 2018, which claims priority from U.S. Provisional Application No. 62/581,789, filed on Nov. 6, 2017, all of which being incorporated herein by reference in their entirety.

TECHNICAL FIELD OF THE INVENTION

The invention generally relates to the field of algae cultivation in artificial conditions and more precisely using geothermal gas a source for $CO_2$ in algae cultivation.

BACKGROUND OF THE INVENTION

Bio-reactors for algae cultivation in artificial conditions has become increasingly common for producing biomass. Algae (or microalgae)-water culture is introduced into a container comprising water and supplied (e.g., fed) with small bubbles of gas that includes $CO_2$ and air. The algae in the container is further exposed to illumination (either artificial illumination, or from sunlight). For the algae biomass to perform photosynthesize and grow, the $CO_2$ needs to be dissolved into the water surrounding the algae culture. In phototropic algae cultivation systems the major inputs (or macro-nutrients) for growth are light, $CO_2$, nutrients (such as Nitrogen, Phosphorus, etc.), and water with turbulent mixing in order to distribute those resources to individual algae cultivation cells.

Microalgae can be grown in many types of systems, such as flat panel photo-bio-reactors having efficient light capture and utilization, and high surface area-to-volume ratio. Light sources for algae growth can be any type of visible light in the range of about 400-700 nm wavelengths. Light emitting diodes (LEDs) have the capability of providing light of specific wavelengths, for example in the visible light (e.g., blue and/or red) wavelength range.

The $CO_2$/air mixture is form by mixing $CO_2$ reach gas (e.g., above 50 weight percent (wt. %) $CO_2$) and air. The mixture usually includes 10-30 wt. % $CO_2$. The gas mixture is introduced as small bubbles into the algae-water culture in the reactor. The portion of the gas not dissolved or consumed by the algae is released into the outside atmosphere. Only a very small portion of the $CO_2$ is consumed by the algae, therefore the majority of $CO_2$ is being released and wasted.

There are several resources for $CO_2$. $CO_2$ reach gas can be obtained by distillation from air or combustion of carbon based fuels such as methane. $CO_2$ reach gas may include gas that have more than 50 wt. % $CO_2$, for example, more than 80 wt. %, more than 85 wt. % and above. Another source for $CO_2$ may be partially purified geothermal gas. Geothermal gas contains, for example, about 74 wt. % $CO_2$ but is also highly contaminated with toxic gasses such as 23.32 wt. % $H_2S$ and explosive gasses such as 0.81 wt. % hydrogen, and 0.34 wt. % methane. Therefore, geothermal gas cannot be mixed with air to avoid explosion. Furthermore, due to the toxicity of some of the gasses in the geothermal gas, introducing such toxic gasses into an algae culture may have undesired effect on the growth of algae. Even relatively purified geothermal gas still contains 0.79 wt. % $H_2S$ and 2.16 wt. % hydrogen, which makes it problematic to be used as a provider of $CO_2$ for algae cultivation.

Some studies indicate advantageous effects of $H_2S$ on algal growth. For example, Meier et al. 2018 (Removal of $H_2S$ by a continuous microalgae-based photosynthetic biogas upgrading process, Process Safety and Environmental Protection, 119: 65-68) suggest that $H_2S$ may represent an indirect source of sulfur. Some algal strains were successfully used for $H_2S$ removal from biogas, and in some cases gas input containing $H_2S$ was found to be beneficial for algal growth. Ramirez-Rueda et al. 2020 (The effect of chemical sulfide oxidation on the oxygenic activity of an alkaliphilic microalgae consortium deployed for biogas upgrading, Sustainability 2020, 12, 6610) observed a 85% enhancement in oxygenic photosynthetic activity (indication of growth) of an alkaliphilic microalgae consortium, when the media sulfide concentration was 16 mg/L (irradiances of 120 µE/m2 s, 30° C., and pH of 8.5).

Some studies investigated the dependence of tolerance and absorption of $H_2S$ on the algal (and other) species, cultivation conditions (light, temp, pH, dissolved oxygen) and $H_2S$ content in the input gas. Küster et al. 2005 (Effects of hydrogen sulfide to *Vibrio fischeri*, *Scenedesmus vacuolatus*, and *Daphnia magna*. Environ. Toxicol. Chem. 2005, 24, 2621-2629) studied the toxicity of sulfide in the cultivation of *Scenedesmus* sp. and reported that at 2 mg/L, the growth rate decreased by 50%. Gonzalez-Camejo et al. 2017 (Short and long-term experiments on the effect of sulphide on microalgae cultivation in tertiary sewage treatment. Bioresour. Technol. 2017, 244, 15-22) found that a concentration of 5 mg/L reduced the oxygen production (corresponding with photosynthetic activity) rate by 43% during the cultivation of *Scenedesmus* sp. when exposed to 300 µE/m² s at 24° C. Moreover, González-Sánchez and Posten 2017 (Fate of $H_2S$ during the cultivation of *Chlorella* sp. deployed for biogas upgrading. J. Environ. Manag. 2017, 191, 252-257) noted that in the initial stages of batch cultivation, the growth of *Chlorella* sp. was completely inhibited by dissolved $H_2S$ at 16 mg/L. However, they observed that after two days, the chemical oxidation of $H_2S$ improved the growth of *Chlorella* sp. by the formation of sulfate, which was subsequently assimilated in the microalgae cells. Svavarsson et al. 2017 (Environ Technol 2018 August; 39(16):2097-2104) reported a successful cultivation of blue-green algae using geothermal power plant gas containing 2% vol $H_2S$. At pH>8, the sulfides $H_2S(L)$ and hydrosulfide (HS—) oxidized in the presence of oxygen by both chemical and biological reactions (see González-Sánchez, A.; Revah, S. The effect of chemical oxidation on the biological sulfide oxidation by an alkaliphilic sulfoxidizing bacterial consortium. Enzym. Microb. Technol. 2007, 40, 292-298), where the kinetic of the chemical sulfide oxidation was assumed to follow a first order respect to sulfide and 0.2 respect to $O_2$ (Nielsen et al. 2003, Determination of kinetics and stoichiometry of chemical sulfide oxidation in wastewater of sewer networks. Environ. Sci. Technol. 2003, 37, 3853-3858). Therefore, $H_2S$ absorption at pH>8 would exponentially increase the dissolved sulfide concentration as the pH arises. On the other hand, under intensive oxygenic photosynthetic activities, the dissolved oxygen (DO) could accumulate in the photobioreactor culture broth above 20 mg/L (Toro-Huertas, E. I et al. 2019, Photorespiration in an outdoor alkaline open-photobioreactor used for biogas upgrading. Sci. Total Environ. 2019, 667, 613-621). The increased concentrations of dissolved $H_2S$ and $O_2$ would enhance the chemical sulfide oxidation in agreement with Nielsen et al. 2003 (Determination of kinetics and stoichiometry of chemical sulfide oxidation in wastewater of sewer networks. Environ. Sci. Technol. 2003, 37, 3853-3858) and then impact the metabolism of microalgae: i.e., the growing rate and oxygen production activity.

Accordingly, in order to use geothermal gas in algae cultivation a special system and method is required.

SUMMARY OF THE INVENTION

Some aspects of the invention may be related to a method of growing algae in a cultivation container. In some embodiments, the method may include: circulating, via the cultivation container, in a closed loop, a first predetermined amount of gas mixture comprising a first type of gas and at least one second type of gas, the gas mixture enters the container via one or more entrance spargers and exit via at least one exit pipe, wherein the first type of gas contains $CO_2$ at a known first amount; receiving signal indicative of the amount of $CO_2$, in the gas mixture; when the signal indicates that the amount of $CO_2$ drops below a first predetermined level, extracting a second predetermined amount of the gas mixture from the cultivation container: and adding an amount of the first type of gas to the gas mixture, equal to the second predetermined amount.

In some embodiments, the method may include: circulating, via the cultivation container, in a closed loop, a first predetermined amount of gas mixture comprising a first type of gas and at least one second type of gas, where the gas mixture enters the container via one or more entrance spargers and exit via at least one exit pipe, wherein the first type of gas contains $CO_2$ at a known first amount; receiving signal indicative of the amount of $H_2S$, in the gas mixture; when the signal indicates that the amount of $H_2S$ rises above a first predetermined level, extracting a second predetermined amount of the gas mixture from the cultivation container: and adding an amount of the first type of gas to the gas mixture, equal to the second predetermined amount. Alternatively or complementarily, after receiving the signal indicative of the amount of $H_2S$ in the circulating gas mixture, the method may comprise replacing the circulating gas mixture with a new first predetermined amount of the gas mixture when the amount of $H_2S$ rises above a second predetermined level.

$H_2S$ levels are significant because if $H_2S$ levels are too high this can cause death of the algae, hinder algae growth, and/or cause the algae to have a foul odor. Accordingly, in case $H_2S$ levels are detected to rise above the first predetermined level, at least part of the circulating gas mixture may be replaced with a gas mixture having a lower level or no $H_2S$, and/or a gas mixture having a lower level or no $H_2S$ may be added to the circulating gas to lower the level of $H_2S$ in the resulting new mixture of recirculating gas.

In some embodiments, the first type of gas may further include a toxic gas at a known second amount. In some embodiments, the first type of gas may be a geothermal gas. In some embodiments, the first known amount may be at least 9 weight % $CO_2$. In some embodiments, the second type of gas may include $N_2$. In some embodiments, the method may further include receiving signal indicative of the amount of $O_2$ in the circulating gas mixture; and replacing the circulating gas mixture with a new first predetermined amount of the gas mixture when the amount of $O_2$ raised above a second predetermined level.

Some aspects of the invention include an algae cultivation system, including: a cultivation container having one or more entrance spargers for introducing a gas mixture into the cultivation container and an exit pipe for releasing the gas mixture from cultivation container; a circulating system for circulating the gas mixture in closed loop form the exit pipe back to the one or more entrance spargers; at least one sensor for detecting changes in an amount of $CO_2$ in the gas mixture and a first gas supply system for supplying a first type of gas. In some embodiments, the first type of gas may include $CO_2$ at a known first amount. In some embodiments, the system may further include: a second gas supply system for supplying a second type of gas; and a controller configured to: control the first gas supply system and the second gas supply system to supply to the circulating system a first predetermined amount of gas mixture comprising the first type of gas and second type of gas; receive from the sensor a signal indicative of the amount of $CO_2$ in the gas mixture; and when the signal indicates that the amount of $CO_2$ drops below a first predetermined level, open a valve to extract a second predetermined amount of the gas mixture from the cultivation container; and control the first gas supply system to supply to the circulating system the first type of gas in an amount equal to the second predetermined amount.

Some aspects of the invention may be related to an algae cultivation system, the system may include: a cultivation container having one or more entrance spargers for introducing a gas mixture into the cultivation container and an exit pipe for releasing the gas mixture from cultivation container; a circulating system for circulating the gas mixture in closed loop form the exit pipe back to the one or more entrance spargers; at least one sensor for detecting changes in an amount of $H_2S$ in the gas mixture and a first gas supply system for supplying a first type of gas. In some embodiments, the first type of gas may include $CO_2$ at a known first amount. In some embodiments, the system may further include: a second gas supply system for supplying a second type of gas; and a controller configured to: control the first gas supply system and the second gas supply system to supply to the circulating system a first predetermined amount of gas mixture comprising the first type of gas and second type of gas; receive from the sensor a signal indicative of the amount of $H_2S$ in the gas mixture; and when the signal indicates that the amount of $H_2S$ rises above a first predetermined level, open a valve to extract a second predetermined amount of the gas mixture from the cultivation container; and control the first gas supply system to supply to the circulating system the first type of gas in an amount equal to the second predetermined amount.

In some embodiments, each of the first and the second gas supply systems may include a valve controlled by the controller. In some embodiments, the system may further include a third gas supply system for providing substantially pure $CO_2$. In some embodiments, the at least one sensor is one of: pH sensor located at the cultivation container and $CO_2$ and/or $H_2S$ sensor located in a circulation pipe included in the circulation system.

In some embodiments, the algae cultivation system may further include an $O_2$ sensor for detecting changes in an amount of $O_2$ in the circulating gas mixture. In some embodiments, the controller may further be configured to: receive a signal indicative of the amount of $O_2$ in the circulating gas mixture; when the amount of $O_2$ raised above a second predetermined level, control a relive valve included in the circulation system to release the circulating gas mixture; and control the first gas supply system and the second gas supply system to supply to the circulating system the first predetermined amount of gas mixture comprising the first type of gas and second type of gas.

In some embodiments, the first type of gas further may include a toxic gas at a known second amount. In some embodiments, the first type of gas may be a geothermal gas. In some embodiments, the first known amount may be at least 9 weight % of $CO_2$. In some embodiments, the second type of gas contains $N_2$.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
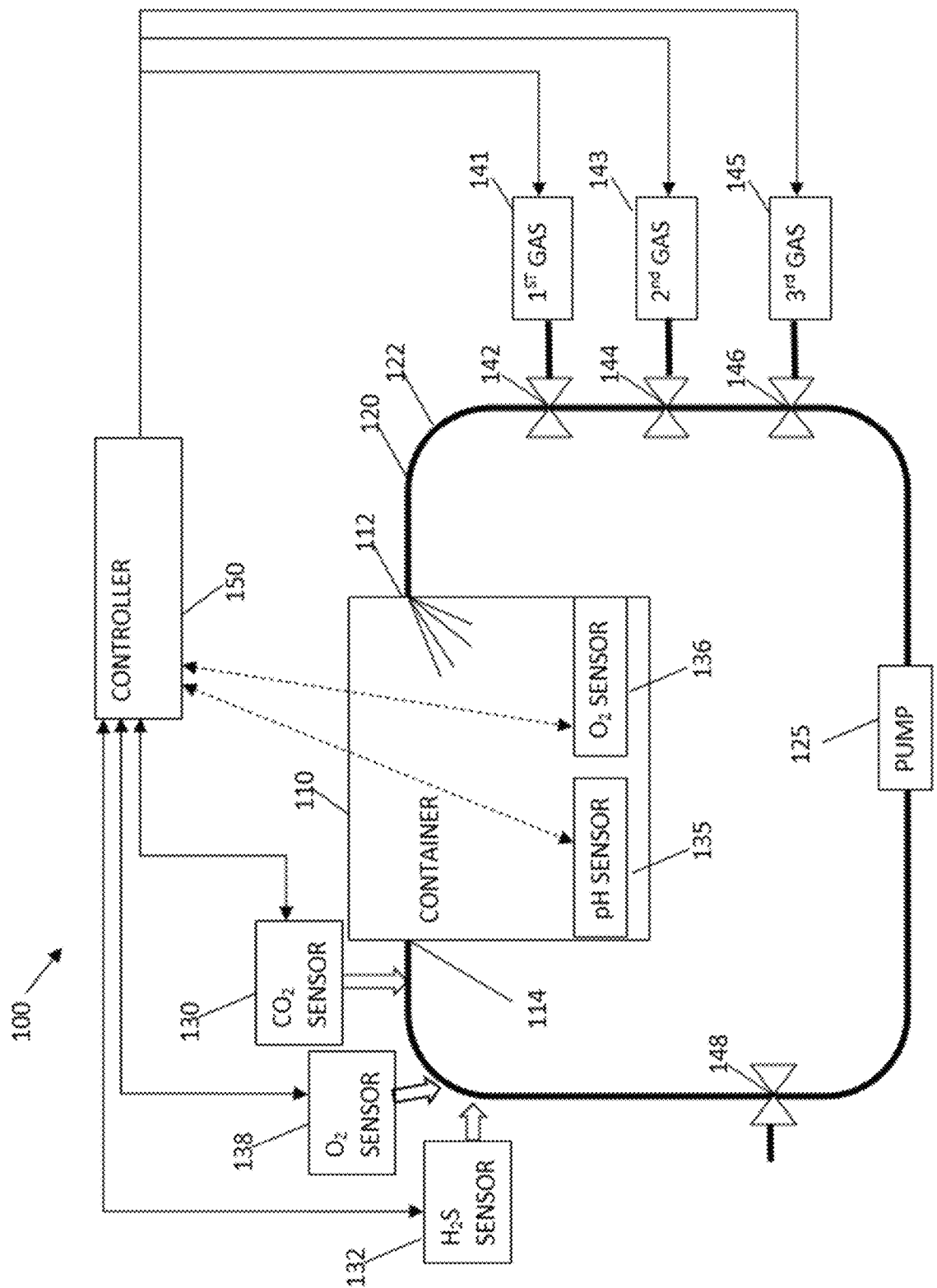
FIG. 1 is an illustration of an algae cultivation system according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Reference is now made to FIG. 1, which schematically illustrates an algae cultivation system 100, according to some embodiments of the invention. System 100 may include a cultivation container 110 having one or more entrance spargers 112 for introducing gas into an algae culture and water located inside cultivation container 110 and an exit pipe 114 for releasing gas from cultivation container 110. System 100 may further include a circulating system 120 that includes a pipe 122 and a pump 125 for circulating gas in closed loop form the exit pipe 114 back to the one or more entrance spargers 112. System 100 may further include, at least one sensor 130, 132, 138 in circulating system 120 and at least one sensor 135, 136 inside cultivation container 110 for detecting signals indicative of the amount of a first type of gas (e.g., $CO_2$, $H_2S$, $O_2$), and two or more gas supply systems 141, 143 and 145 for providing a first type of gas, a second type of gas and/or a third type of gas to circulation system 120. For example, signals may be received, which are indicative of the amounts of $CO_2$ and/or $H_2S$, in the mixture. In some embodiments, the system may include a relief valve 148 for relieving gas from circulation system 120. In some embodiments, system 100 may include one or more $O_2$ sensors 136 and 138 for detecting changes in an amount of $O_2$ in the circulating gas mixture.

It is noted that while literature sources are equivocal concerning the effects of $H_2S$ on algal growth, the inventors have found out that in disclosed algal growth systems, especially disclosed systems for growing cyanobacteria such as *Arthrospira* spp. (e.g., *Arthrospira platensis*) for producing spirulina extracts, the level of sulfides (dissolved $H_2S$) should be monitored and if needed modified to prevent damage (lethal or sublethal) to the algae and moreover, prevent sulfide traces yielding bad sulfuric smell in the algal products, such as spirulina extracts. For example, under typical growth conditions (temperatures between 25° C. and 35° C., e.g., 30° C. or intermediate values; pH between 9 and 11, e.g., 9.5, 10 or 10.5, or intermediate values; and illumination intensity between 500 $\mu E/m^2$ and 1000 $\mu E/m^2$, e.g., 600 $\mu E/m^2$, 700 $\mu E/m^2$, 800 $\mu E/m^2$, 900 $\mu E/m^2$ or intermediate values) the level of sulfides ($S^{2-}$ of dissolved $H_2S$) may be kept below a threshold between 0.1 and 1 mg/l, e.g., any of 0.2 mg/l, 0.5 mg/l, 0.7 mg/l or intermediate values, to prevent sublethal and smell effects. It is noted that these thresholds relate to the sulfide concentration in the liquid of the cultivation container, and the first predetermined level of gaseous $H_2S$ may be determined respectively. It is further noted that although the $H_2S$ dissolution rate in liquid depends on multiple variables (e.g., the $H_2S$ concentration in the gas phase, the dissolved $H_2S$ level in the liquid, the temperature, the pH, the bubble size, the residence time, the oxidation level, etc.), in a steady state algal cultivation system with consistent growth conditions, the $H_2S$ (gas) concentration is correlated with dissolved sulfide concentration. The exact thresholds may be determined with respect to the product, monitored by the controllers disclosed herein, and sulfide levels may be reduced by mixing or replacing at least some of the gas in the system to a gas with a lower or no $H_2S$ content, as disclosed herein.

In some embodiments, system 100 may further include a controller 150 configured to receive signals from sensor(s) 130, 132 and/or 138 and/or sensor(s) 135 and/or 136 and control valves 142-146 to open and allow gas supply systems 141, 143 and 145 to supply one or more of the first, second and third types of gasses to circulation system 120.

In some embodiments, container 110 may be any algae cultivation container known in the art. For example, container 110 may include at least two panels (not illustrated) within a water filled cultivation container 110, the panels positioned along a first plane the first plane is perpendicular to the gravitational force. In some embodiments, a cultivation volume may be created between each pair of panels, whereby the cultivation volumes may be fluidly coupled to allow horizontal flow therebetween along the first plane.

In some embodiments, one or more entrance spargers 112 may each include a plurality of nozzles, to distribute gas (e.g., $CO_2$, geothermal gas and/or air mixture) into cultivation container 110. In some embodiments, the gas bubbles may have a diameter of no more than 5 mm, for example, 2 mm or 1 mm. One or more entrance spargers 112 may supply the gas mixture to the container at 0.5-3 litter/minute for every liter of algae culture. In some embodiments, the bubbles may be introduced at a flow capacity sufficient for cleaning the walls of container 110 from biofilm covering the walls. In some embodiments, exit pipe 114 may include any device for collecting or extracting gasses from containers. Circulating system 120 may include one or more pipes 122 and any number of required connectors, valves, faucets and the like that may be required to allow forming a closed structure (a loop) for circulating gas form exit pipe 114 back to one or more entrance spargers 112. Circulating system 120 may include a pump 125 or a compressor or blower for evacuating the gas from the upper portion of container 110.

$CO_2$ sensor 130 and/or $H_2S$ sensor 132 may be any sensor configured to detect $CO_2$ and/or $H_2S$, respectively. For example, sensor(s) 130, 132 may be an infrared gas sensor (NDIR), a chemical gas sensor and the like. Sensor 135 may be any sensor that may provide further indication to the amount of $CO_2$ or $H_2S$ in the algae culture, for example, sensor 135 may include a pH sensor. As the amount of $CO_2$ dissolve in the algae culture decrease below a required level the pH level may raise above a harmful level, which depends from the type of algae grow in cultivation container 110 (e.g., pH 7.5). Therefore, the pH may serve as an indicator to the amount of $CO_2$ in the gas mixture.

$O_2$ sensors 136 and 138 may be any sensors that may provide indication to the amount of $O_2$ in the gas mixture. Sensor 136 may be located at circulating container 110 configured to measure the amount of $O_2$ dissolved in the algae culture. Sensor 138 may be any chemical sensor configured to measure the amount of $O_2$ in the circulating gas mixture and may be located in pipe 122.

First gas supply system 141 may be configured to supply a first type of gas, containing $CO_2$ at a known first amount, for example, a geothermal gas or a partially purified geothermal gas. First gas supply system 141 may be in fluid communication with a reservoir (e.g., a tank, a pipe, etc.) that includes the first type of gas. In some embodiments, first gas supply system 141 may include valve 142, controlled by controller 150 and configured to supply the first type of gas to pipe 122 at a predetermined amount. In some embodiments, the known first amount may be at least 9 wt. % or more of $CO_2$. In some embodiments, the first type of gas may further include a toxic gas at a known second amount. For example, a partially purified geothermal gas may include up to 0.79 wt. % $H_2S$ and 2.16 wt. % hydrogen. $H_2S$ and/or hydrogen may be toxic to the algae and a system and method according to embodiments of the invention may be configured to control the amount of provided toxic gases to be below the toxicity level, for example, by continuous circulating the partially purified geothermal gas to cause maximum consumption of $CO_2$ by the algae without providing additional toxic gases, thus increase the level of toxicity to above a harming level. At least one of the sensors may be configured to monitor a concentration of the toxic gas in the algae cultivation system, and the controller may be further configured to reduce the concentration if it crosses a predefined threshold.

Second gas supply system 143 may be configured to supply a second type of gas, for example, a gas containing nitrogen, such as air, nitrogen and the like. In some embodiments, second gas supply system 143 may include valve 144, controlled by controller 150 and configured to supply the second type of gas, for example, at a predetermined amount.

Third gas supply system 145 may be configured to supply a third type of gas, for example, a substantially pure $CO_2$ (e.g., a gas containing at least 90% $CO_2$). In some embodiments, third gas supply system 144 may include valve 146, controlled by controller 150 and configured to supply the third type of gas, for example, at a predetermined amount.

In some embodiments, only one or two types of gasses may be supplied via the one or more gas supply systems 141, 143 and 145. In such embodiments, some of gas supply systems may not be active, or may be operated to provide the same gas or gasses as another supply system. For example, gas supply systems 141 and 143 may supply a first type of gas and system 145 may supply a second type of gas. In another example, supply system 145 may not be operated, while each of supply systems 141 and 143 may supply a different type of gas.

Controller 150 may be any computation platform that is configured to perform instructions to control various components in system 100. Controller 150 may include a processor and a memory to store thereon instructions according to embodiments of the invention. Controller 150 may be configured to: control the first gas supply system to supply to the circulating pipe a first type of gas at a predetermined amount. For example, the controller may be configured to control supply system 141 to supply partially purified geothermal to pipe 120. and control second gas supply system 143 to supply to circulating pipe 120 the second type of gas for example, air or nitrogen. The first type of gas and the second type of gas may be supplied, to pipe 120, to form a first predetermined amount of gas mixture containing the first type of gas and second type of gas. The relative amounts of the first type of gas and the second type of gas, in the gas mixture, may also be predetermined, for example, based on the type of the algae growing in cultivation container 110. In some embodiments, the gas mixture may include (after mixing) at least 5 wt. % $CO_2$ The gas mixture may continually be circulated via container 110, by pump 125. During the circulation at least a portion of the small gas bubbles may dissolve into the water in container 110 and the $CO_2$ may be consumed by the algae. Therefore, in time the amount of the $CO_2$ may be reduced.

Controller 150 may further receive from sensor(s) 130, 132 and/or sensor 135 signal indicative to the amount of the $CO_2$ and/or $H_2S$ in the gas mixture. Controller 150 may continuously monitor the level of the $CO_2$ and/or $H_2S$ as the gas mixture being circulated via container 110. In some embodiments, when the amount of the $CO_2$ drops below a first predetermined level and/or the amount of $H_2S$ rises above a first predetermined level, controller 150 may open valve 148 to extract a second predetermined amount of the gas mixture from the cultivation container, and may then control first gas system 141 to supply the first type of gas in an amount equal to the second predetermined amount. For example, when the pH signal raised above 7.5, indicating that the amount of $CO_2$ is too low, controller 150 may control first gas system 141 to supply geothermal gas having 50% $CO_2$ to pipe 122. Alternatively, controller 150 may control third gas supply system 145 to supply $CO_2$ instead of geothermal gas.

In some embodiments, supplying controlled amounts of geothermal gas, may not harm the algae culture inside container 110 and may eliminate the risk of explosion.

Figure 2:
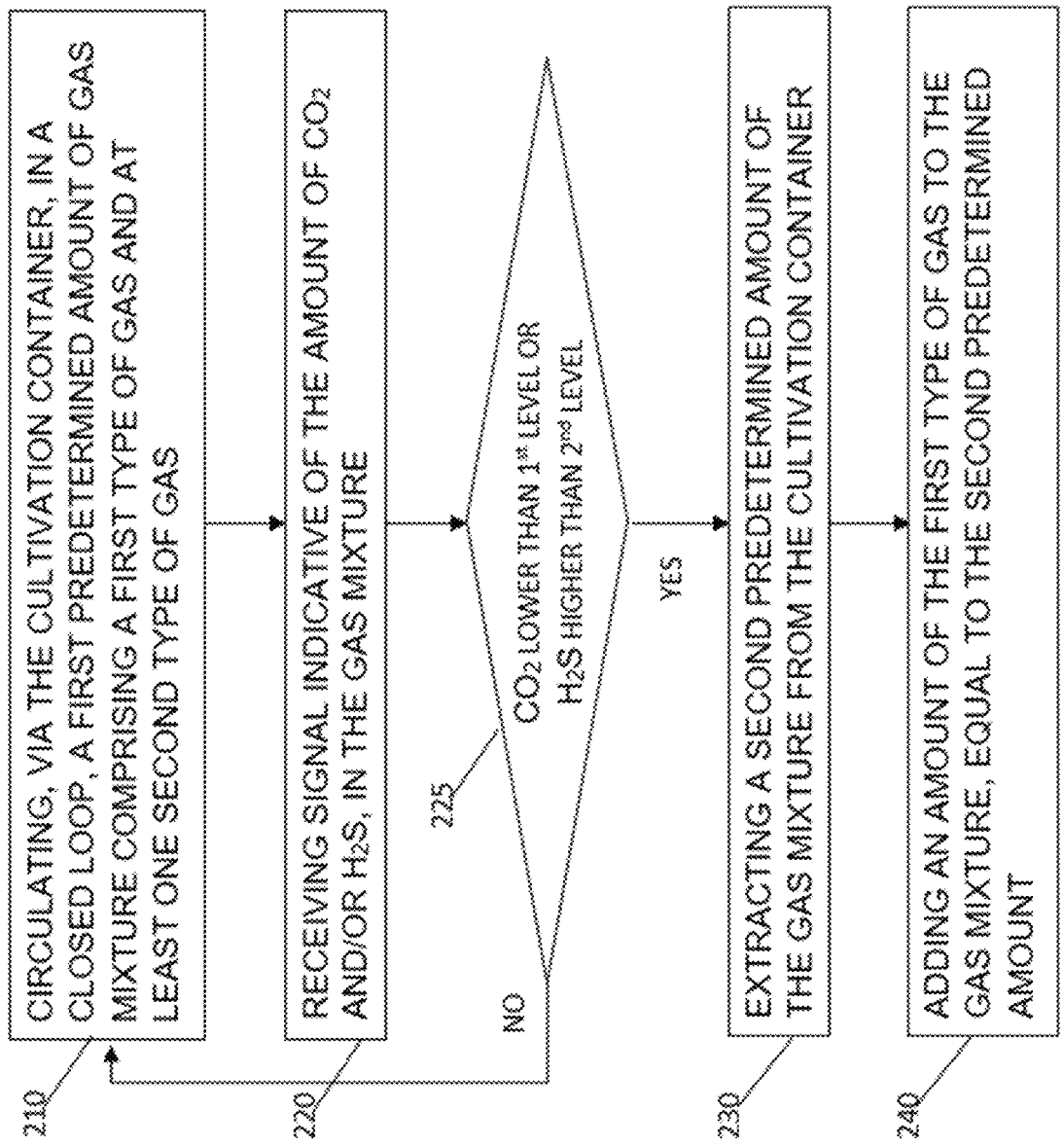
FIG. 2 is a flowchart of a method of growing algae in a cultivation container according to some embodiments of the invention.

Reference is now made to FIG. 2 which is a flowchart of a method of growing algae in a cultivation container using, for example, geothermic gas, according to some embodiments of the invention. In box 210, a first predetermined amount of gas mixture comprising a first type of gas and at least one second type of gas, may be circulated, via a container (e.g., container 110), in a closed loop. In some embodiments, the gas mixture may enter the container via one or more entrance spargers (e.g., spargers 112) and exit via at least one exit pipe (e.g., exit pipe 114). For example, a mixture including a first type of gas containing known amount of $CO_2$ (e.g., geothermal gas containing at least 9 wt. % $CO_2$) and air may be circulated via a container (e.g., a bio-reactor) holding algae (e.g., micro-algae) and water. The entrance spargers may spray the gas mixture to form small bubbles having a diameter of no more than 5 mm, for example, 1 mm. In some embodiments, the first predetermined amount of gas mixture may be circulated continuously to allow consumption of the $CO_2$ from at least the first type of gas. In some embodiments, the first type of gas may include a toxic gas at a known second amount, for example, $H_2S$ or hydrogen included in the geothermal gas. In some embodiments, the continuous circulation may allow the algae to consume the $CO_2$ from the geothermal gas before an additional amount of geothermal gas containing toxic gas(es) has to be added.

In some embodiments, the second type of gas may include gas containing $N_2$, such as, air. The second type of gas may provide the required bubbling and circulation for the algae culture, while the first type of gas may provide the nutrition, in the form of $CO_2$. In some embodiments, the ratio between the first type of gas and second type of gas in the gas mixture may be predetermined, for example, based on the type of algae. For example, the gas mixture may include at least 5% $CO_2$. The first predetermined amount may be determined to provide sufficient $CO_2$ and sufficient mixing and turbulence of the algae culture in container 110.

In box 220, signal indicative of the amount of $CO_2$ or $H_2S$, in the gas mixture may be received. For example, sensor 130 may continually measure the amount of $CO_2$ or $H_2S$ in pipe 122 and a controller such as controller 150 may monitor the measured amount. Additionally or alternatively, sensor 135 may monitor the pH level in container 110, the pH level may be indicative to the amount of $CO_2$ in the algae culture and the gas mixture.

If the signal indicative of the amount of $CO_2$ shows that the amount dropped below a predetermined level 1 or if the signal indicative of the amount of $H_2S$ shows that the amount rose above a predetermined level 2 (box 225—YES), then in box 230, a second predetermined amount of the gas mixture from the cultivation container may be extracted to re-established required levels of $CO_2$ and $H_2S$ with respect to their thresholds. In some embodiments, controller 150 may control valve 148 to open and extract from circulation system 120, the second predetermined amount of gas mixture. The extracted gas mixture may have less relative amount of $CO_2$ or a higher relative amount of $H_2S$ with respect to the gas mixture initially supplied in box 210. For example, 0.5 liters of circulated gas mixture per liter culture may be extracted when the pH of the algae culture reaches 7.5.

Following the extraction (e.g., after controller 150 closed valve 148) an amount of the first type of gas may be added to the gas mixture, in box 240. The added amount may be equal to the second predetermined amount. For example, controller 150 may control first gas system 141 to add 0.5 liters of geothermal gas per liter culture to circulation system 120.

In some embodiments, the process may continue until the amount of $O_2$ in the gas mixture and/or the algae capture reached a second predetermined level, for example, 35 wt. %. During the photosynthesis process the algae consumes the $CO_2$ and produces $O_2$ which above a certain amount prevents further grow of the algae. In some embodiments, the method may include replacing the circulating gas mixture with a new first predetermined amount of the gas mixture when the amount of $O_2$ raised above a second predetermined level. For example, controller 150 may control relive valve 148 to release the circulating gas mixture entirely. In this release all toxic gases accumulated in the circulating gas mixture are released as well. Following the release controller 150 may control first gas supply system 141 and the second gas supply system 143 to supply to the circulating system the first predetermined amount of gas mixture comprising the first type of gas and second type of gas, thus repeating the step in box 210.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of growing algae in a cultivation container, the method comprising:
   circulating, via the cultivation container, in a closed loop, a first predetermined amount of gas mixture comprising a first type of gas and at least one second type of gas, the gas mixture enters the container via one or more entrance spargers and exit via at least one exit pipe, wherein the first type of gas contains $CO_2$ at a known first amount;
   receiving at least one signal indicative of the amounts of $CO_2$ and $H_2S$, in the gas mixture;
   when the at least one signal indicates that the amount of $H_2S$ rises above a first predetermined level, extracting a second predetermined amount of the gas mixture from the cultivation container; and
   adding an amount of the first type of gas to the gas mixture, equal to the second predetermined amount.

2. The method of claim 1, wherein the first type of gas further comprises a toxic gas at a known second amount.

3. The method of claim 2, wherein the first type of gas is a geothermal gas.

4. The method of claim 1, wherein the first known amount is at least 9 weight % $CO_2$.

5. The method of claim 1, wherein the second type of gas contains $N_2$.

6. The method of claim 1, further comprising, when the at least one signal indicates that the amount of $CO_2$ drops below a first predetermined level:
   extracting a second predetermined amount of the gas mixture from the cultivation container; and
   adding an amount of the first type of gas to the gas mixture, equal to the second predetermined amount.

7. The method of claim 1, further comprising:
   receiving at least one signal indicative of the amount of $CO_2$ in the circulating gas mixture; and
   replacing the circulating gas mixture with a new first predetermined amount of the gas mixture when the amount of $CO_2$ drops below a second predetermined level.

8. The method of claim 1, further comprising:
   receiving at least one signal indicative of the amount of $H_2S$ in the circulating gas mixture; and
   replacing the circulating gas mixture with a new first predetermined amount of the gas mixture when the amount of $H_2S$ rises above a second predetermined level.

9. The method of claim 1, wherein the first predetermined level corresponds to a sulfide concentration of 1 mg/l in liquid of the cultivation container.

10. The method of claim 1, wherein the first predetermined level corresponds to a sulfide concentration of 0.5 mg/l in liquid of the cultivation container.

11. An algae cultivation system, comprising:
    a cultivation container having one or more entrance spargers for introducing a gas mixture into the cultivation container and an exit pipe for releasing the gas mixture from cultivation container;

a circulating system for circulating the gas mixture in closed loop form the exit pipe back to the one or more entrance spargers;

at least one sensor for detecting changes in an amount of $CO_2$ and $H_2S$ in the gas mixture;

a first gas supply system for supplying a first type of gas, wherein the first type of gas contains $CO_2$ at a known first amount;

a second gas supply system for supplying a second type of gas; and a controller configured to:

control the first gas supply system and the second gas supply system to supply to the circulating system a first predetermined amount of gas mixture comprising the first type of gas and second type of gas;

receive from the sensor a signal indicative of the amount of $H_2S$ in the gas mixture; and when the signal indicates that the amount of $H_2S$ rises above a first predetermined level, open a valve to extract a second predetermined amount of the gas mixture from the cultivation container; and control the first gas supply system to supply to the circulating system the first type of gas in an amount equal to the second predetermined amount.

12. The algae cultivation system of claim 11, wherein each of the first and the second gas supply systems comprises a valve controlled by the controller.

13. The algae cultivation system of claim 11, further comprising a third gas supply system for providing substantially pure $CO_2$.

14. The algae cultivation system of claim 11, wherein the at least one sensor is one of: pH sensor located at the cultivation container and $H_2S$ sensor located in a circulation pipe included in the circulation system.

15. The algae cultivation system of claim 11, wherein the controller is further configured to receive from the sensor a signal indicative of the amount of $CO_2$ in the gas mixture; and when the signal indicates that the amount of $CO_2$ drops below a first predetermined level, open a valve to extract a second predetermined amount of the gas mixture from the cultivation container.

16. The algae cultivation system of claim 11, further comprising:

an $O_2$ sensor for detecting changes in an amount of $O_2$ in the circulating gas mixture; and wherein the controller further configured to:

receive a signal indicative of the amount of $O_2$ in the circulating gas mixture;

when the amount of $O_2$ raised above a second predetermined level, control a relive valve included in the circulation system to release the circulating gas mixture; and control the first gas supply system and the second gas supply system to supply to the circulating system the first predetermined amount of gas mixture comprising the first type of gas and second type of gas.

17. The algae cultivation system of claim 11, wherein the first type of gas further comprises a toxic gas at a known second amount, and wherein at least one of the sensors is configured to monitor a concentration of the toxic gas in the algae cultivation system, wherein the controller is further configured to reduce the concentration if it crosses a predefined threshold.

18. The algae cultivation system of claim 17, wherein the first type of gas is a geothermal gas.

19. The algae cultivation system of claim 11, wherein the first predetermined level corresponds to a sulfide concentration of between 0.1 and 1 mg/l in liquid of the cultivation container.

20. The algae cultivation system of claim 11, wherein the second type of gas contains $N_2$.

* * * * *